(12) United States Patent
Pilz et al.

(10) Patent No.: US 10,012,630 B2
(45) Date of Patent: Jul. 3, 2018

(54) HYDROLYSIS-STABLE MESOPOROUS SILICA MATERIAL AND METHOD FOR PRODUCING IT

(71) Applicant: Robert Bosch GmbH, Stuttgart (DE)

(72) Inventors: Thomas Pilz, Leonberg (DE); Markus Widenmeyer, Schoenaich (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 15/099,033

(22) Filed: Apr. 14, 2016

(65) Prior Publication Data

US 2016/0304541 A1 Oct. 20, 2016

(30) Foreign Application Priority Data

Apr. 14, 2015 (DE) .................... 10 2015 206 619

(51) Int. Cl.
C07F 7/02 (2006.01)
G01N 33/00 (2006.01)
C07F 7/18 (2006.01)

(52) U.S. Cl.
CPC ........... *G01N 33/004* (2013.01); *C07F 7/188* (2013.01); *C07F 7/1836* (2013.01)

(58) Field of Classification Search
CPC ...... G01N 33/004; C07F 7/1836; C07F 7/188
USPC ....................................................... 556/408
See application file for complete search history.

(56) References Cited

U.S. PATENT DOCUMENTS

2004/0213996 A1* 10/2004 Fujiwara ................ A61K 9/143
428/402

OTHER PUBLICATIONS

Wahab et al., J. Nanosci. Nanotechnol. 2011, 11(10):8481-7.*
Wang et al., Chem. Soc. Rev., 2009, 38, 1315-1329.*
Wahab et al., Hydrothermally Stable Periodic Mesoporous Ethane-Silica and Bimodal Mesoporous Nanostructures, Journal of Nanosciece and Nanotechnology, 2011, pp. 8481-8487, vol. 11, American Scientific Publishers, United States of America.
Barrett et al.; The Determination of Pore Volume and Area Distributions in Porous Substances. I. Computations from Nitrogen Isotherms; J. Am. Chem. Soc.; Jan. 1951; pp. 373-380, vol. 73.
Gorka, J. et al, "Mesoporous metal organic framework-boehmite and silica composites", ChemCommun., The Royal Society of Chemistry, 2010, 3 pages.

* cited by examiner

*Primary Examiner* — Fereydoun G Sajjadi
*Assistant Examiner* — Kofi Adzamli
(74) *Attorney, Agent, or Firm* — Walter Ottesen, P.A.

(57) ABSTRACT

A hydrolysis-stable mesoporous silica material has surface bearing functional groups of formula $O_xSiR_{4-x}$, where x is in a range from 1-3 and where each of the radicals R independently of any other contains c carbon atoms, n nitrogen atoms and o oxygen atoms, for which $$\frac{c+n}{o} > 0.35.$$

At least ⅓ of the nitrogen atoms and of the oxygen atoms carries in each case at least one hydrogen atom or is ionic. At least one radical R of a functional group is crosslinked with another radical R of a different functional group. The material is produced by providing a mesoporous silica material and functionalizing the surface of the mesoporous silica material with at least one silane of formula $Y_xSiR_{4-x}$, where x is in a range from 1-3 and where Y is a functional group which reacts with a hydroxyl group on the surface of the mesoporous silica material. There is crosslinking of the surface functionalities by treatment with a coupling reagent having at least two reactive groups, each reactive group reacting with a radical R.

26 Claims, 4 Drawing Sheets

HYDROLYSIS-STABLE MESOPOROUS SILICA MATERIAL AND METHOD FOR PRODUCING IT

This application claims priority under 35 U.S.C. § 119 to patent application number DE 10 2015 206 619.3, filed on Apr. 14, 2015 in Germany, the disclosure of which is incorporated herein by reference in its entirety.

BACKGROUND

The present disclosure relates to a hydrolysis-stable mesoporous silica material and to a method for producing the hydrolysis-stable mesoporous silica material. The present disclosure further relates to the use of the hydrolysis-stable mesoporous silica material as sensor material.

Surface-functionalized mesoporous silica materials can be used for sensor applications in water-containing gases. The pores of these functionalized materials have functional groups with the capacity to undergo basic reaction with water. As a result it is possible to determine, for example, the carbon dioxide content of the water-containing gas, by using electrodes mounted on the functionalized material to measure changes in the electrical properties of the material. This application requires the incorporation of liquid water into the pores by means of capillary condensation. With materials of these kinds, however, the risk exists of the Si—O—Si bonds, which produce the firm attachment to the pore surface of the organic functionalities that are needed for hydrophilization of the pore surface, undergoing hydrolysis and in this way the organic functionalities possibly become detached. A further risk lies in the hydrolyzability of the $SiO_2$ pore structure, since many of these materials have very thin pore walls only a few $SiO_2$ molecule layers thick.

For the purpose of improving the hydrolysis resistance of the silane framework, Wahab M. A. and Ciabin H. in "Hydrothermally stable periodic mesoporous ethane-silica and bimodal mesoporous nanostructures", J. Nanosci. Nanotechnol. 2011, October; 11(10):8481-7, proposed joining two (—O)$_3$Si units to one another via a short organic group. In this case, in addition to the aforementioned statistical effect, there is also an increase in the hydrophobicity of the framework. With measures of this kind it would be possible generally to achieve hydrolysis stability for such sensor materials. It is nevertheless necessary, moreover, to achieve the required chemical properties of the material, namely the hydrophilicity of its pore surface and the base functionality.

SUMMARY

The hydrolysis-stable mesoporous silica material in accordance with the disclosure has functional groups of the formula $O_xSiR_{4-x}$ on its surface. In this formula, x is in the range from 1 to 3. Each of the radicals R, independently of one another, contains c carbon atoms, n nitrogen atoms and o oxygen atoms. For these it is the case according to formula 1 that:

$$H = \frac{c+n}{o} > 0.35 \quad \text{(formula 1)}$$

Through fulfillment of the condition that H>0.35, the functional groups have strongly hydrophilic or hygroscopic properties. It is in fact preferred for H>0.40. If o=0, the condition of formula 1 is always met.

At least a third of the nitrogen atoms and of the oxygen atoms carries in each case at least one hydrogen atom or is ionic. This likewise contributes to the strong hydrophilicity of the functional groups. A particularly high hydrophilicity can be achieved if at least one of the nitrogen atoms is a nitrogen atom of a tetraalkylammonium function.

At least one radical R of a functional group is crosslinked with another radical R of a different functional group. This produces high stability of the functional groups. The higher the value of x, the more pronounced the additional stabilization of the functional groups.

Whereas the functional groups for x=1 are only monopodal, it is preferred for x to adopt a value in the range from 2 to 3, and so the functional groups are at least bipodal. More preferably x has a value of 3, and so all functional groups are tripodal. By each functional group being crosslinked at least with a further functional group, even monopodal functional groups are joined via at least two oxygen atoms to the surface of the silica material. Bipodal functional groups are joined via at least four oxygen atoms to the surface of the silica material, and tripodal functional groups are joined in fact via at least six oxygen atoms to the surface of the silica material.

A mesoporous silica material in accordance with the IUPAC definition is a material having a pore diameter in the range from 2 nm to 50 nm. This pore diameter can be determined by means of the Barrett-Joyner-Halenda (BJH) method, which is described in E. P. Barret, L. G. Joyner, P. P. Halenda, J. Am. Chem. Soc. 1951, 73, 373. The hydrolysis-stable mesoporous silica material preferably has a number-average pore diameter in the range from 2 nm to 10 nm Materials with a pore diameter of this kind are especially suitable for sensor applications.

The crosslinking is preferably via 1-hydroxy-2-amino groups and/or via carboxamido groups. Groups of these kinds are stable to hydrolysis and can be prepared in the presence of silica materials under reaction conditions under which the framework of the silica materials is not hydrolyzed.

The surface of the mesoporous silica material that is functionalized with the functional groups of the formula $O_xSiR_{4-x}$ preferably has $O_3Si$—X—$SiO_3$ units. In this formula, X is selected from alkylene groups and/or arylene groups. Particularly preferred alkylene groups are methylene and ethylene. A particularly preferred arylene group is phenylene. A mesoporous silica material of this kind is particularly stable with respect to hydrolysis of its functionalities as a result of the multipodal attachment of its functionalities to the surface of the material, and, furthermore, additionally exhibits increased stability relative to hydrolysis of its framework.

The hydrolysis-stable mesoporous silica material can be used as sensor material, especially for determining the carbon dioxide content of a fluid.

The method of the disclosure for producing a hydrolysis-stable mesoporous silica material comprises the following steps:

providing a mesoporous silica material,
functionalizing the surface of the mesoporous silica material with at least one silane of formula $Y_xSiR_{4-x}$, where x is in the range from 1 to 3 and where Y is a functional group which reacts with a hydroxyl group on the surface of the mesoporous silica material,
crosslinking the surface functionalities by treatment with a coupling reagent which has at least two reactive groups, each reactive group reacting with a radical R.

Each of the radicals R independently of any other contains c carbon atoms, n nitrogen atoms and o oxygen atoms, with the formula 1 applying. At least a third of the nitrogen atoms and of the oxygen atoms carries in each case at least one hydrogen atom or is ionic.

In order to produce a silica material that is especially suitable for sensor applications, it is preferred for the mesoporous silica material which is provided to have a number-average pore diameter (BJH) in the range from 2 nm to 10 nm. For this purpose it is preferred, moreover, for the mesoporous silica material provided to have a BET surface area in the range from 500 $m^2/g$ to 1500 $m^2/g$. The pore system of the silica material provided is preferably regular.

In order to ensure particularly high stability to hydrolysis on the part of the framework of the hydrolysis-stable mesoporous silica material, it is preferred for the surface of the mesoporous silica material to have $O_3Si$—X—$SiO_3$ units, where X is selected from alkylene groups and/or arylene groups.

It is preferred for Y to be an alkoxy group. A methoxy group is particularly preferred in this context. Groups Y of these kinds are especially suitable as leaving groups for the functionalization of the surface of the mesoporous silica material provided.

The molar ratio between the silane and the coupling reagent is preferably at least 2:1. This ensures that each molecule of the coupling reagent actually enters into a coupling reaction with at least two silane molecules. Each molecule of the coupling reagent which reacts only with one single silane molecule would not lead to any crosslinking of functional groups. Where the coupling reagent has more than two reactive groups, reaction conditions are in fact provided in this way under which the coupling reagent is able to crosslink more than two silane molecules with one another, thus achieving particularly secure attachment of the functionalities to the surface of the hydrolysis-stable mesoporous silica material.

In one embodiment of the method at least one reactive group is an epoxide group which reacts with an amino group in a radical R of a surface functionality. In this case a 1-hydroxy-2-amino unit is formed which represents the concrete linking unit between the linked silane molecules.

In another embodiment of the method the at least one reactive group is an amino group which reacts with a haloalkyl group or a carbonyl halide group in a radical R of a surface functionality. For this purpose the coupling reagent is preferably very highly hydrophilic.

In this embodiment it is preferred for the haloalkyl group or the carbonyl halide group to be generated on the surface functionality after the surface of the mesoporous silica material has been functionalized.

With the method it is possible for more silane equivalents to be attached to the surface of the silica material than actually correspond to the equivalents of SiOH groups on the surface. Silanes fixed through the organic crosslinking may crosslink additionally via their SiOH groups as a result of subsequent treatment in a humid atmosphere. Since individualized Si—O—Si bonds on the surface may open as a result of the influence of water, such groups are likewise able to react with free SiOH groups of excess silanes. This produces a high density of organic functionalities and an increased stability on the part of the framework.

BRIEF DESCRIPTION OF THE DRAWINGS

Exemplary embodiments of the disclosure are shown in the drawings and elucidated in more detail in the description hereinafter.

DETAILED DESCRIPTION

Figure 1:
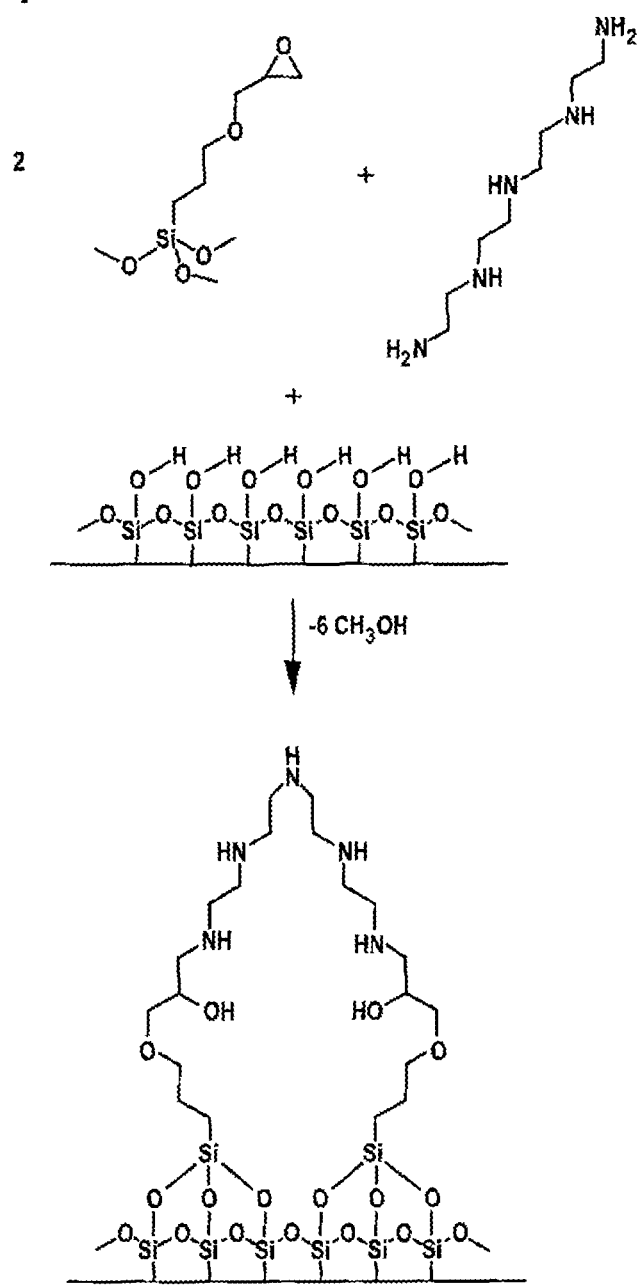
FIG. 1 shows a reaction scheme for the production of a hydrolysis-stable mesoporous silica material according to one exemplary embodiment of the disclosure.

In a first exemplary embodiment of the disclosure, 1 g of a MCM-48 material (Mobile Composition of Matter No. 48) having a pore diameter of 4.5 nm and a SiOH group density of 3 mmol/g is reacted with 3 mmol of 3-glycidyloxypropyltrimethoxysilane and 1 mmol of tetraethylenepentamine in toluene for eight hours at a temperature of 100° C. 3-glycidyloxypropyltrimethoxysilane is a silane of formula $Y_xSiR_{4-x}$ with Y=$CH_3O$ and R=$(CH_2)_3OCH_2(CHOH)CH_2$. According to formula 1, c=6, n=0,O=2, H=3. According to the reaction scheme shown in FIG. 1, with elimination of methanol, a hydrolysis-stable mesoporous silica material is formed that has two respectively tripodal functionalities crosslinked to one another. On its surface it has functionalities of formula $O_xSiR_{4-x}$ with x=1. For this, according to formula 1, H=3. The radicals R of each pair of functionalities are crosslinked via $NH(CH_2)_2NH(CH_2)_2NH(CH_2)_2NH(CH_2)_2NH$ groups in such a way that for the resulting group, which joins two Si atoms to one another, according to formula 1, c=20, n=5, O=4, H=6.25. This product is isolated by filtration and dried for two hours at a temperature of 80° C. in the air. The many hydroxyl groups and amine groups in vicinal arrangement (connected via two carbon atoms) give the hydrolysis-stable mesoporous silica material a high hydrophilicity. A material functionalized in this way is highly suitable for applications requiring amine groups in a hydrophilic environment, as is required, for example, for determining the $CO_2$ content of a fluid.

Figure 2:
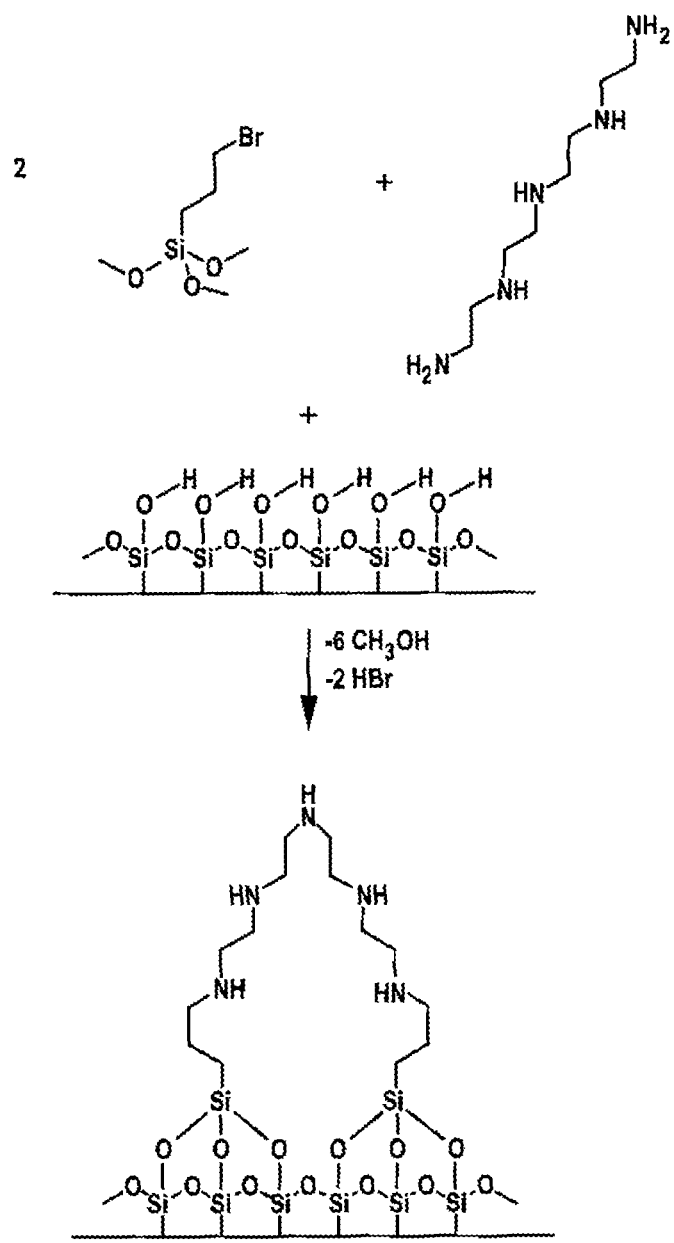
FIG. 2 shows a reaction scheme for the production of a hydrolysis-stable mesoporous silica material according to another exemplary embodiment of the disclosure.

In a second exemplary embodiment of the disclosure, 1 g of the MCM-48 material which was used as a reactant in the first exemplary embodiment of the disclosure as well is reacted with 3 mmol of bromopropyltrimethoxysilane ($Y_xSiR_{4-x}$ with Y=$CH_3O$ and R =$(CH_2)_3Br$, where according to formula 1 c=3, n=0, o=0) and 1 mmol of tetraethylenepentamine in toluene for eight hours at a temperature of 100° C. and then worked up as in the first exemplary embodiment. In accordance with the reaction scheme shown in FIG. 2, with elimination of methanol and hydrogen bromide, a hydrolysis-stable mesoporous silica material is formed for which according to formula 1 c=13, n=5, o=0. In contrast to the material according to the first exemplary embodiment of the disclosure, this material has no hydroxyl groups, instead having only vicinally arranged amine functionalities. These functionalities, however, are sufficient to endow the material likewise with a hydrophilicity such that it is suitable for the sensor application according to the first exemplary embodiment of the disclosure.

Figure 3:
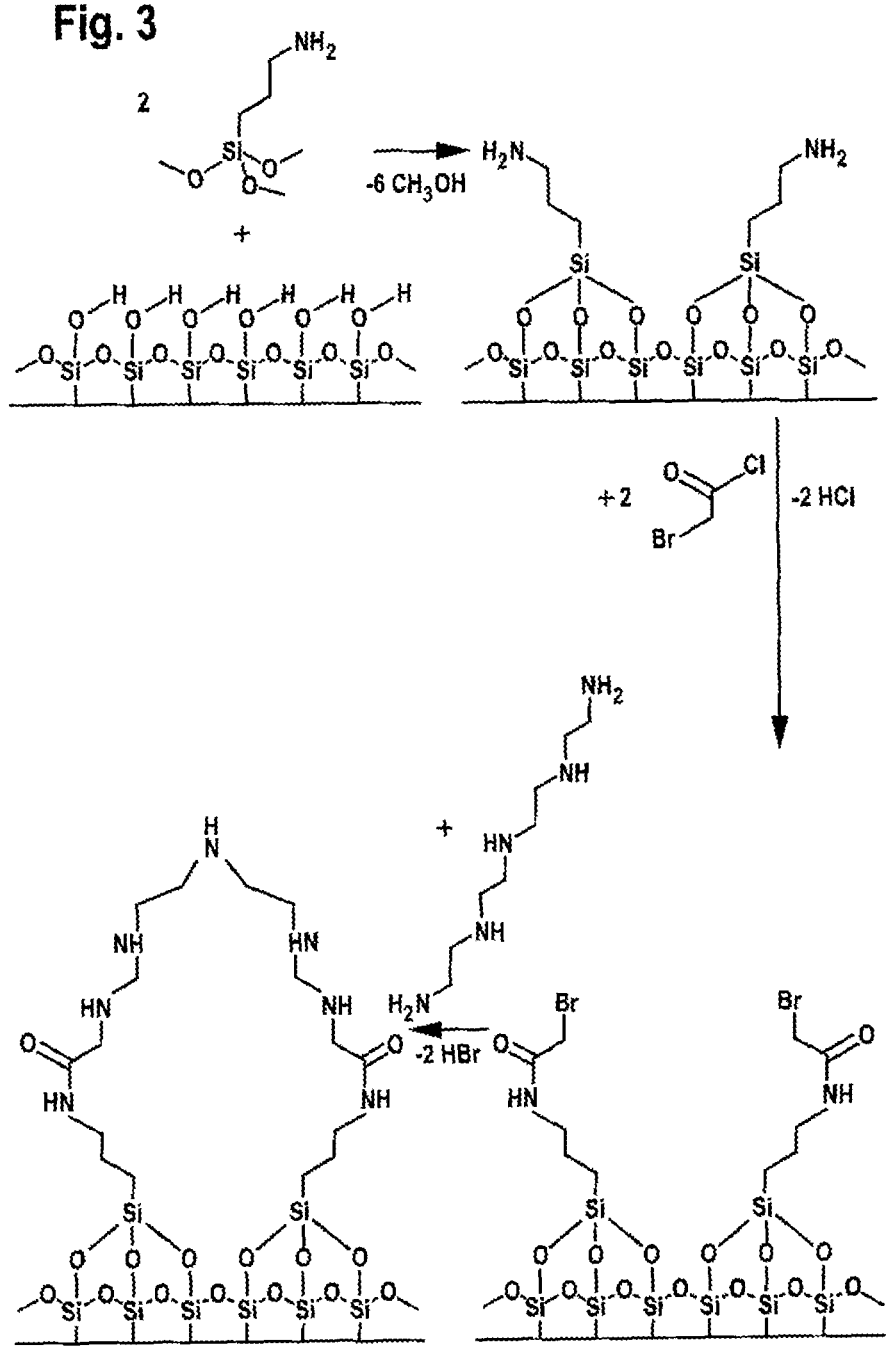
FIG. 3 shows a reaction scheme for the production of a hydrolysis-stable mesoporous silica material according to yet another exemplary embodiment of the disclosure.

In a third exemplary embodiment of the disclosure, 1 g of the MCM-48 material is first functionalized with 3 mmol of aminopropyltrimethoxysilane. As shown in the reaction scheme shown in FIG. 3, there is a surface functionalization accompanied by elimination of methanol. Subsequently the material thus functionalized is reacted with 3 mmol of bromoacetyl chloride. With elimination of hydrogen chloride, this generates acyl bromide groups on the functionalities. Lastly there is a reaction with 1 mmol of tetraethylenepentamine. This leads, with elimination of hydrogen bromide and with formation of amide bonds, to a crosslinking of the tripodal silane functionalities. In this way as well a hydrolysis-stable mesoporous silica material is obtained that has a high number of vicinally arranged amine groups, this material having a highly hydrophilic pore surface and therefore being suitable for the sensor applications already described. For this product, in accordance with formula 1 c=20, n=5, o=2, H=7.5.

Figure 4:
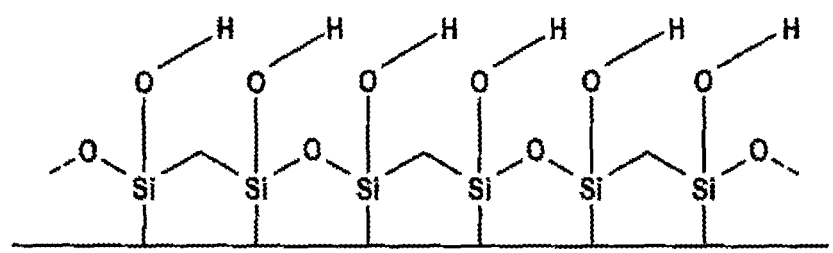
FIG. 4 shows schematically a mesoporous silica material which can be used as reactant in a method according to an exemplary embodiment of the disclosure.

In all of the exemplary embodiments of the disclosure it is possible, rather than the MCM-48 material, to use a mesoporous silica material whose Si—O—Si bonds have been wholly or partly replaced by Si—Y—Si groups in which Y is an alkylene or arylene group. FIG. 4 shows by way of example a material of this kind in which 50% of the oxygen atoms in the surface Si—O—Si groups have been replaced by methylene groups. The preparation of a material of this kind is described in Wahab M. A., Ciabin H. "Hydrothermally stable periodic mesoporous ethane-silica and bimodal mesoporous nanostructures", J. Nanosci. Nanotechnol. 2011, October; 11(10):8481-7. Such materials exhibit particularly high framework stability.

What is claimed is:

1. A hydrolysis-stable mesoporous silica material whose surface bears functional groups of the formula $O_xSiR_{4-x}$,
    wherein x is in a range from 1 to 3,
    wherein each R independently comprises c carbon atoms, n nitrogen atoms and o oxygen atoms,
    wherein
    $$\frac{c+n}{o} > 0.35,$$
    wherein at least a third of the nitrogen atoms and of the oxygen atoms are bound to in each case at least one hydrogen atom or are ionic, and
    wherein at least one R of one of the functional groups is crosslinked with another R of a different functional group.

2. The hydrolysis-stable mesoporous silica material according to claim 1, wherein the material has a number-average pore diameter in a range from 2 nm to 10 nm.

3. The hydrolysis-stable mesoporous silica material according to claim 1, wherein the crosslinking is via 1-hydroxy-2-amino groups and/or via carboxamido groups.

4. The hydrolysis-stable mesoporous silica material according to claim 1, wherein the surface of the mesoporous silica material functionalized with the functional groups of the formula $O_xSiR_{4-x}$ has $O_3Si$—X—$SiO_3$ units, where X is selected from alkylene groups and/or arylene groups.

5. The hydrolysis-stable mesoporous silica material according to claim 1, wherein the material is used as sensor material.

6. The hydrolysis-stable mesoporous silica material according to claim 1, wherein the mesoporous silica material has a BET surface area in a range from 500 m²/g to 1500 m²/g.

7. The hydrolysis-stable mesoporous silica material according to claim 1, wherein the functional groups are crosslinked with a coupling reagent comprising at least two reactive groups, and:

wherein at least one reactive group is an epoxide group which reacts with an amino group of R of the functional group,
and/or
wherein at least one reactive group is an amino group which reacts with a haloalkyl group or a carbonyl halide group of R of the functional group.

8. The hydrolysis-stable mesoporous silica material according to claim 7, wherein the haloalkyl group or the carbonyl halide group is generated on the functional group after functionalization of the surface of the mesoporous silica material.

9. A hydrolysis-stable mesoporous silica material whose surface is functionalized with at least one silane functional group of the formula $Y_xSiR_{4-x}$,
    wherein x is in the range from 1 to 3,
    wherein Y is a functional group which reacts with a hydroxyl group on the surface of the mesoporous silica material,
    wherein each R independently comprises c carbon atoms, n nitrogen atoms and o oxygen atoms,
    wherein
    $$\frac{c+n}{o} > 0.35,$$
    wherein at least a third of the nitrogen atoms and of the oxygen atoms are bound to in each case at least one hydrogen atom or are ionic, and
    wherein at least one R of one of the functional groups is crosslinked with another R of a different functional group.

10. The hydrolysis-stable mesoporous silica material of claim 9, wherein Y is an alkoxy group.

11. The hydrolysis-stable mesoporous silica material according to claim 9, wherein the functional groups are crosslinked with a coupling reagent comprising at least two reactive groups, and wherein a molar ratio between the at least one silane group and the coupling reagent is at least 2:1.

12. The hydrolysis-stable mesoporous silica material according to claim 1, wherein at least one of the nitrogen atoms is a nitrogen atom of a tetraalkylammonium function.

13. The hydrolysis-stable mesoporous silica material according to claim 1, wherein x is in a range from 2 to 3.

14. The hydrolysis-stable mesoporous silica material according to claim 1, wherein x is 3.

15. The hydrolysis-stable mesoporous silica material according to claim 4, wherein X is a methylene group, an ethylene group, or a phenylene group.

16. The hydrolysis-stable mesoporous silica material according to claim 10, wherein Y is a methoxy group.

17. The hydrolysis-stable mesoporous silica material according to claim 1, wherein the at least one R of one of the functional groups is crosslinked with the R of a different functional group via a $NH(CH_2)_2NH(CH_2)_2NH(CH_2)_2NH(CH_2)_2NH$ group.

18. A method for producing a hydrolysis-stable mesoporous silica material, comprising:
    providing a mesoporous silica material;
    functionalizing a surface of the mesoporous silica material with at least one silane of formula $Y_xSiR_{4-x}$, where x is in the range from 1 to 3 and where Y is a functional group which reacts with a hydroxyl group on the surface of the mesoporous silica material; and crosslinking the surface functionalities by treatment with a coupling reagent which has at least two reactive groups, each reactive group reacting with a radical R;

where each of the radicals R independently of any other contains c carbon atoms, n nitrogen atoms and o oxygen atoms, for which $$\frac{c+n}{o} > 0.35,$$

at least a third of the nitrogen atoms and of the oxygen atoms carrying in each case at least one hydrogen atom or being ionic.

19. The method according to claim 18, wherein the mesoporous silica material has a BET surface area in a range from 500 m²/g to 1500 m²/g.

20. The method according to claim 18, wherein the mesoporous silica material has a number-average pore diameter in a range from 2 nm to 10 nm.

21. The method according to claim 18, wherein the surface of the mesoporous silica material has O₃Si—X—SiO₃ units, where X is selected from alkylene groups and/or arylene groups.

22. The method according to claim 18, wherein Y is an alkoxy group.

23. The method according to claim 18, wherein a molar ratio between the at least one silane and the coupling reagent is at least 2:1.

24. The method according to claim 18, wherein at least one reactive group is an epoxide group which reacts with an amino group in a radical R of a surface functionality.

25. The method according to claim 18, wherein at least one reactive group is an amino group, which reacts with a haloalkyl group or a carbonyl halide group in a radical R of a surface functionality.

26. The method according to claim 24, wherein the haloalkyl group or the carbonyl halide group is generated on the surface functionality after the surface of the mesoporous silica material has been functionalized.

* * * * *